United States Patent [19]
Akiyama

[11] 4,078,305
[45] Mar. 14, 1978

[54] SURGICAL THREAD AND CUTTING APPARATUS FOR THE SAME

[76] Inventor: Taichiro Akiyama, 19–23, Shimoochai 2-chome, Shinjuku, Tokyo, Japan

[21] Appl. No.: 751,470

[22] Filed: Dec. 17, 1976

Related U.S. Application Data

[62] Division of Ser. No. 653,243, Jan. 28, 1976.

[51] Int. Cl.² .............................................. B26B 13/26
[52] U.S. Cl. .................................... 30/134; 140/123.6
[58] Field of Search .................. 30/131, 134, 233, 249, 30/250, 251; 140/123.6

[56] References Cited

U.S. PATENT DOCUMENTS

| 1,125,366 | 1/1915 | Meitz | 30/131 |
| 1,920,056 | 7/1933 | Briggs | 30/134 |
| 2,856,686 | 10/1958 | Stanley | 30/131 |
| 3,802,074 | 4/1974 | Hoppe | 30/134 |

Primary Examiner—Jimmy C. Peters
Attorney, Agent, or Firm—McDougall, Hersh & Scott

[57] ABSTRACT

A cutting apparatus for a surgical thread which comprises a thread-like body and a plurality of projections formed at regular intervals in the thread-like body. The cutting apparatus includes a holder for the surgical thread through which the surgical thread is inserted, a cutting member arranged adjacent to the holder, an actuating rod for actuating the cutting member, and a trigger for driving the actuating rod. Even when the blood vessel is ligated with the surgical thread in the interior of the human body, the surgical thread can be easily cut by the cutting apparatus in the interior of the human body.

12 Claims, 6 Drawing Figures

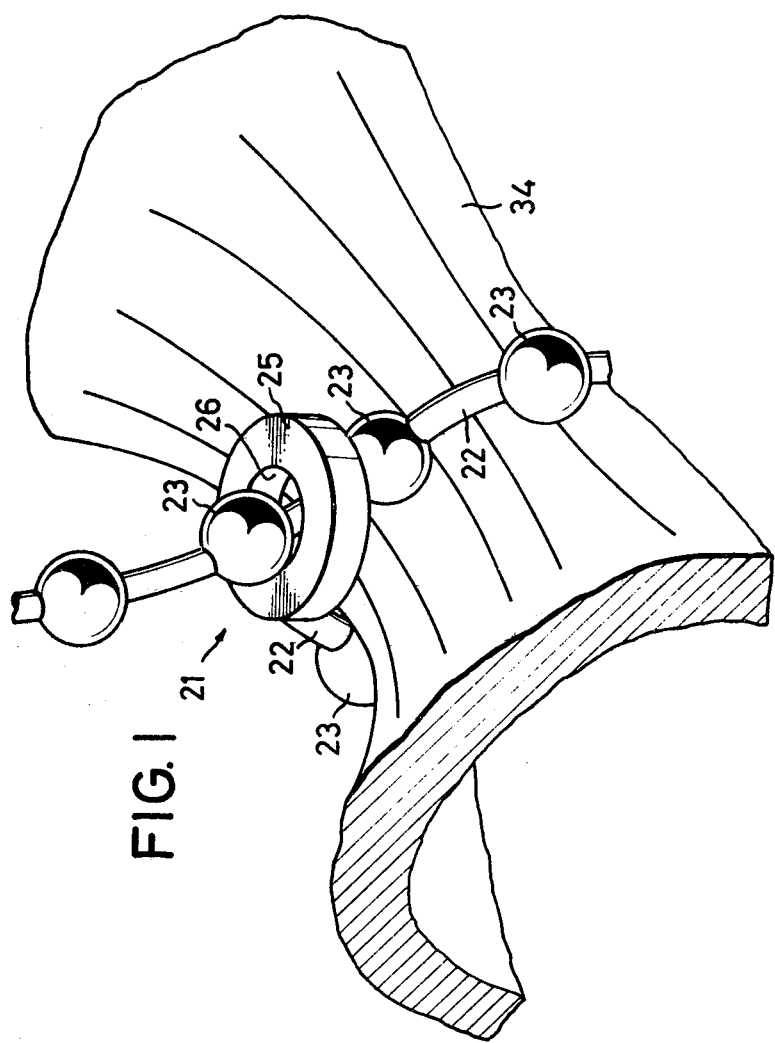

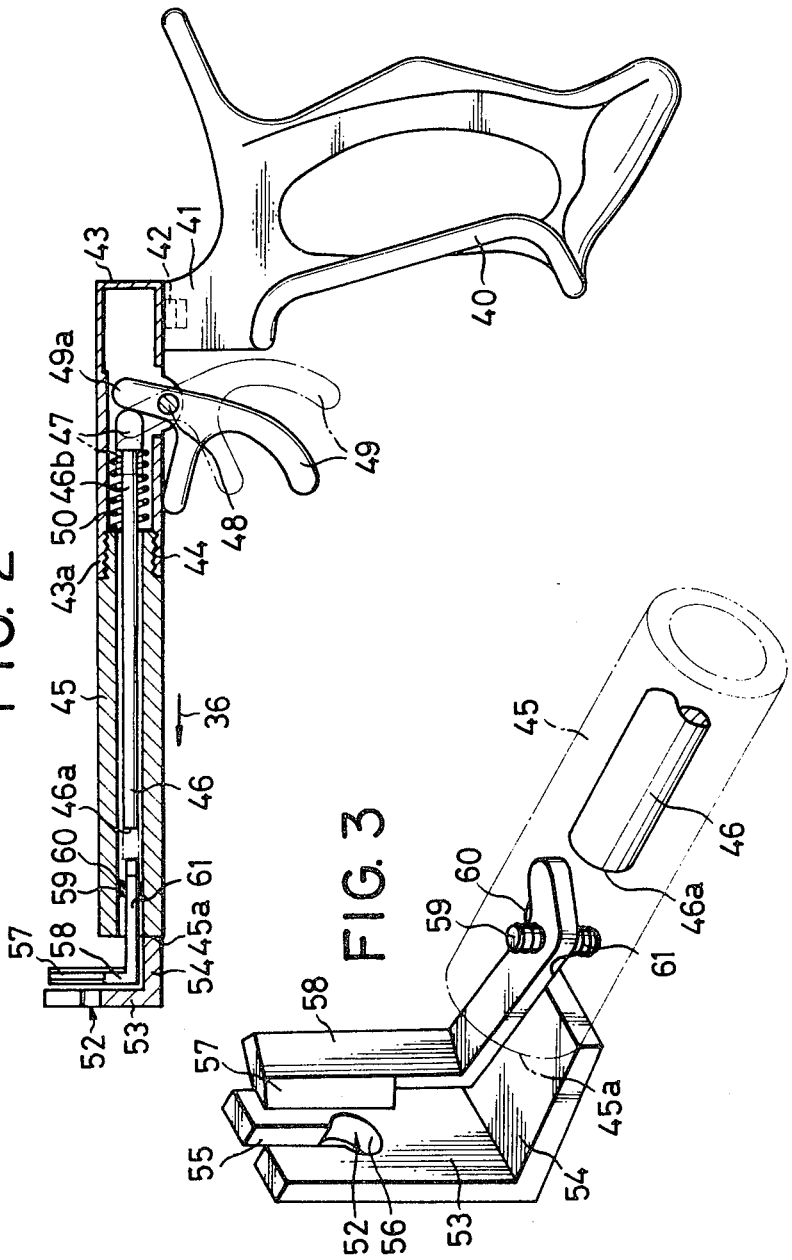

SURGICAL THREAD AND CUTTING APPARATUS FOR THE SAME

This is a division, of application Ser. No. 653,243, filed 1-28-76.

BACKGROUND OF THE INVENTION

1. Field of the Invention

This invention relates to a surgical thread cutting apparatus, the surgical thread being most suitably used as a ligature or a sewing or stitching thread.

2. Description of the Prior Art

Hitherto, a thread or a filament of synthetic resin is widely used as a surgical thread such as a ligature or a sewing or stitching thread. The friction of the surface of such a conventional thread is little. Accordingly, for example, when the blood vessel is ligated with the conventional thread, the knotted thread is apt to loosen. The ligating condition is very unstable. In order to obtain the stable ligating condition, a double knot or a complicated knot of the conventional thread should be made. That is very trouble-some. Even in the double knot, the conventional thread has the disadvantage that the thread ligating the blood vessel is apt to slide in the lengthwise direction of the blood vessel.

SUMMARY OF THE INVENTION

It is an object of this invention to provide a cutting apparatus by which surgical thread can be simply cut, even when the blood vessel positioned inside the incised human body is ligated with the surgical thread without drawing out the blood vessel from the inside of the incised human body.

In accordance with an aspect of this invention, a surgical thread includes a thread-like body and a plurality of projections formed at intervals in the threadlike body.

In accordance with another aspect of this invention, a cutting apparatus for the surgical thread includes a holder for a surgical thread through which the surgical thread is inserted, a cutting member arranged adjacent to the holder, an actuating rod for actuating the cutting member, and a trigger for driving the actuating rod.

The above and other objects, features and advantages of this invention will become apparent from the following detailed description of illustrative embodiments shown in the accompanying drawings.

BRIEF DESCRIPTION OF THE DRAWINGS

FIG. 1 is an enlarged perspective view illustrating surgical thread in association with a blood vessel;

FIG. 2 is a side elevation, partly in section, of the cutting apparatus of this invention;

FIG. 3 is an enlarged perspective view of the principal cutting elements of the apparatus.

DESCRIPTION OF THE PREFERRED EMBODIMENTS

Figure 4:
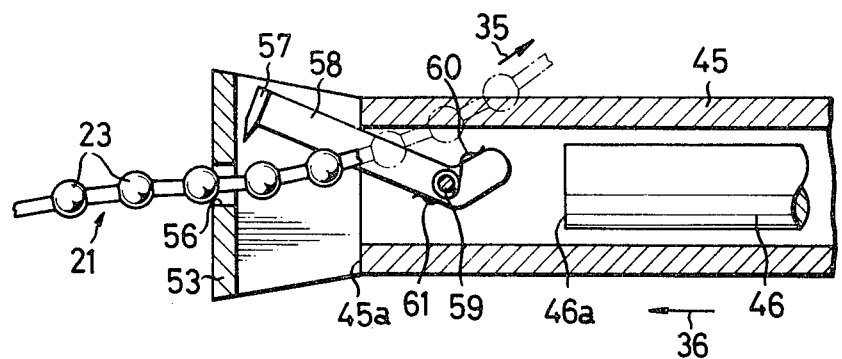
FIGS. 4, 5 and 6 are enlarged fragmentary, cross-sectional views illustrating the cutting apparatus, surgical thread and blood vessel in sequential stages of operation.

Referring to FIG. 1, a ligature 21 comprises a thread 22 and spherical projections 23 formed integrally with the thread 22 at regular intervals. Reference is made to applicant's copending application Ser. No. 653,243, filed on Jan. 28, 1976, for a more detailed description of the surgical thread contemplated for use in association with the cutting apparatus including variations from the thread design illustrated in FIG. 1.

In surgical operation, a part of the human body or the tissue is incised. The blood vessel 34 is exposed or embedded in the tissue or positioned inside the human body. According to the ligature 21, the blood vessel 34 needs not be drawn out from the inside of the human body or from the tissue with hand or a device. First, the hooked needle of the ligature 21 is stuck into the tissue round the blood vessel 34, and it is rotated round the blood vessel 34 by about 180°. As shown by the dot-dash line on FIG. 11, the hooked needle 24 is taken out from the tissue, and so the blood vessel 34 is perfectly caught by the ligature 21.

The hooked needle is further drawn outwardly, and the tip of the hooked needle is inserted through the round hole 26 of the threading member 25.

Figure 5:
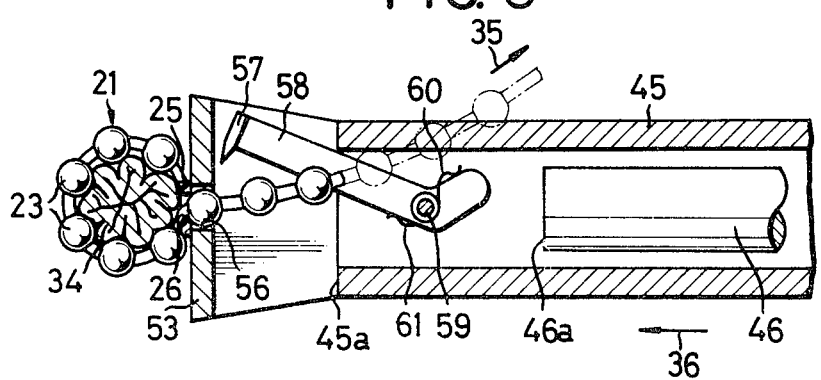
Figure 6:
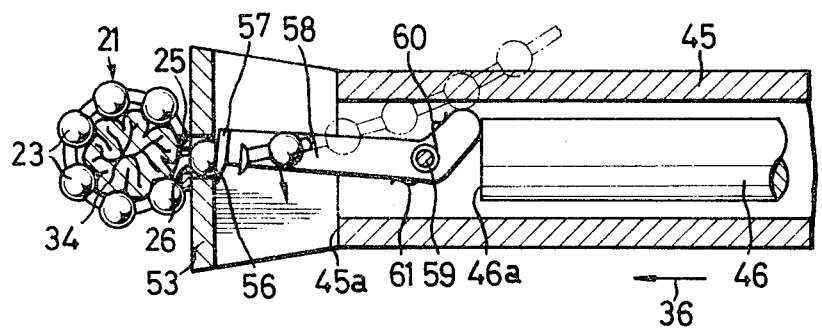

After the hooked needle is inserted through the round hole 26 of the threading member 25, the hooked needle is pulled up in the direction shown by the arrow 35 on FIG. 4, with one hand, while the threading member 25 is pushed down toward the blood vessel 34 in the direction shown by the arrow 36 on FIG. 4, with another hand. The thread 22 and the projections 23 pass through the hole 26 of the threading member 25 to form a loop 37 round the blood vessel 34. The size of the loop 37 is reduced with the pulling-up of the hooked needle. At last, the threading member 25 contacts with the blood vessel 34, and the ligature 21 is wound on the blood vessel 34, as shown in FIGS. 5 and 6.

Further, the threading member 25 is pushed down to squash the blood vessel 34. In that condition, the ligature 21 cannot be more pulled up. Thus, the ligature 21 is tightly wound on the blood vessel 34 to ligate the latter.

In the ligating condition shown, the one projection 23, which has passed through the hole 26, contacts tightly with the upper edge of the threading member 25, while the adjacent other projection 23, which has not yet passed through the hole 26, contacts tightly with the lower edge of the threading member 25. By the frictional forces among the edges of the threading member 25, the projections 23 and the blood vessel 34, the ligature 21 is surely tied round the blood vessel 34, although the hooked needle 24 and the threading member 25 are separated from the hands of the operator. The shape of the threading member 25, and therefore of the hole 26 is slightly changed with the shape of the blood vessel 34. It is more difficult that the projection 23 passes through the deformed hole 26. Accordingly, the ligature 21 is more surely tied round the blood vessel 34. Moreover, since the frictional forces occur between the projections 23 and the blood vessel 34, the ligature 21 cannot slide along the circumference of the blood vessel 34 and in the lengthwise direction of the blood vessel 34.

The ligature 21 is cut off at the desirable position by a below-described cutting apparatus. The bleeding is surely stopped by the ligature 21 wound tightly round the blood vessel 34. The ligating operation is more sure and simple than by the conventional method.

Next, a cutting apparatus for cutting the ligature 21, according to this invention, will be described with reference to FIGS. 2-6.

Referring to FIG. 2 and FIG. 3, a cutting apparatus includes a handle 40 formed of metal or synthetic resin, a cylindrical member 43 formed of metal which is fixed to a top portion 41 of the handle 40 by a screw 42, a cylindrical holder 45 which is fixed to the top 43a of the cylindrical member 43 by a screw 44, an actuating rod 46 formed of metal which is slidably inserted into the cylindrical holder 45, and a trigger 49 formed of metal which contacts at its upper end with a contact member 47 fixed to a rear end 46b of the actuating rod 46 and is pivoted to a pin 48 fixed to the cylindrical member 43.

A coil spring 50 is disposed between the rear end of the cylindrical holder 45 and the contact member 47, for restoring the actuating rod 46. A front end 46a of the actuating rod 46 is withdrawn inward from the front opening 51 of the cylindrical holder 45. A ligature holder 53 having the L-shaped cross section is fixed to the front end 45a of the cylindrical holder 45. A cutout 52 like a key hole is formed in the ligature holder 53. The vertical wall of the ligature holder 53 is distant from the rear end 45a of the cylindrical holder 45 by the length of the horizontal wall 54 of the ligature holder 53. The cutout 52 consists of a rectangular hole 55 and a round hole 56 communicating with the rectangular hole 55. The round hole 56 is designed so that the projections 23 can pass through the hole 56, but the threading member 25 cannot pass through the hole 56. A cutter 58 having a knife edge 57 pararell with the vertical wall of the ligature holder 53 is disposed between the ligature holder 53 and the cylindrical holder 45. The cutter 58 is L-shaped, and its one end is bent, as apparent from FIG. 3, which is rotatably supported by a pin 59 fixed to the cylindrical holder 45. Torsion springs 60 and 61 are wound on the upper end and lower end of the pin 59 to urge the cutter 58 in the clockwise direction, so that one side of the cutter 58 contacts with the front end 45a of the cylindrical holder 45, as shown on FIG. 4 and FIG. 5. When the cutter 58 is rotated in the counter-clockwise direction, the knife edge 57 passes closely by the hole 56 of the ligature holder 53.

Next, operations of the above-described cutting apparatus will be described.

The thread 22 of the ligature 21 between the hooked needle 24 and the loop 37 is put into the round hole 56 of the ligature holder 53 through the rectangular hole 55 thereof. In that condition, the hooked needle 24 is held by one hand of an operator, while the handle 40 of the apparatus is held by another hand of the operator. The hooked needle 24 is pulled in the direction shown by the arrow 35, while the apparatus is moved toward the blood vessel 34 in the direction shown by the arrow 36 on FIG. 4. The ligature 21 successively passes through the round hole 56 of the ligature holder 53. As the result, the threading member 25 of the ligature 21 comes to contact with the ligature holder 53, as shown on FIG. 5. Since the size of the threading member 25 is larger than that of the hole 56, the threading member 25 cannot pass through the hole 56. Accordingly, the threading member 25 is stopped by the ligature holder 53, and only the projections 23 and the thread 22 can pass through the hole 56. When the blood vessel 34 is squashed, the threading member 25 is pressed between the blood vessel 34 and the ligature holder 53, and moreover the ligature holder 53 is positioned inside the human body.

Next, the trigger 49 shown on FIG. 2 is drawn backward to the position shown by the dot-dash line on FIG. 2. The contact member 47 is pushed by the upper end 49a of the trigger 49, so that the actuating rod 46 is moved forward in the direction shown by the arrow 36 within the cylindrical holder 45 against the coil spring 50.

With the movement of the actuating rod 46, the front end 46a of the actuating rod 46 pushes the bent end of the cutter 58 to rotate the cutter 58 in the counter-clockwise direction against the torsion springs 60 and 61. With the rotation of the cutter 58, the ligature 21 is cut off by the knife edge 57 of the cutter 58, as shown on FIG. 6. The more sharp the edge of the hole 56, the easier the cutting of the ligature 21.

Thus, the ligature 21 can be cut off at the desired position in the condition that the blood vessel 34 is surely ligated by the ligature 21 without drawing out from the inside of the human body 33. The tie of the ligature 21, the stop of bleeding and the cutting of the ligature 21 can be successively effected by the apparatus according to this invention. Accordingly, the ligating operation can be remarkably simplified in comparison with the conventional method.

After cutting the ligature 21, the trigger 40 is separated from the hand of the operator. The trigger 40 and the actuating rod 45 is restored to their original positions by the coil spring 50. And the cutter 58 is rotated back to its original position in the clockwise direction by the torsion springs 60 and 61.

Although illustrative embodiments of this invention have been described in detail herein with reference to the accompanying drawings, it is to be understood that the invention is not limited to those precise embodiments, and that various changes and modifications may be effected therein by one skilled in the art without departing from the spirit and scope of the novel concepts of this invention, as defined in the appended claims.

What is claimed is:

1. A cutting apparatus for a surgical thread comprising a thread-like body and a plurality of projections formed at intervals in said thread-like body, said apparatus comprising a holder for said surgical thread through which said surgical thread is inserted, a cutting means arranged adjacent said holder, an actuating rod for actuating said cutting means, and a trigger for driving said actuating rod, said holder defining a rectangular hole and a round hole communicating with said rectangular hole, said surgical thread being inserted into said round hole through said rectangular hole.

2. A cutting apparatus according to claim 1, in which said actuating rod is slidably supported within a cylindrical holder.

3. A cutting apparatus according to claim 2, in which a spring is disposed between one end of said cylindrical holder and a contact member attached to one end of said actuating rod, and one end of said trigger contacts with said contact member.

4. A cutting apparatus according to claim 2, in which said cutting means is rotatably supported by a pin fixed on the inner wall of said cylindrical holder.

5. A cutting apparatus according to claim 2 wherein said holder defines a substantially L-shaped cross-section, the portion of the holder defining said rectangular and round holes being disposed substantially perpendicular to the axis of said actuating rod.

6. A cutting apparatus according to claim 2 wherein said rectangular hole comprises a slot having a width greater than the thickness of said thread-like body and less than the diameter of a projection, said round hole having a diameter of a projection, said round hole having a diameter greater than the diameter of a projection.

7. A cutting apparatus for a surgical thread comprising a thread-like body, a plurality of projections formed at intervals in said thread-like body, a needle member attached to one end of said thread-like body, and a threading member formed on another end of said thread-like body through which said needle member, said thread-like body and said projections can pass to form a loop round an object, some of said projections being fastened with said threading member when said object is held by said loop, said apparatus comprising a holder for said surgical thread through which said surgical thread is inserted, a cutting means arranged adjacent said holder, an actuating rod for actuating said cutting means, and a trigger for driving said actuating rod, said holder defining a rectangular hole and a round hole communicating with said rectangular hole, said surgical thread being inserted into said round hole through said rectangular hole.

8. A cutting apparatus according to claim 7 wherein said holder defines a substantially L-shaped cross-section, the portion of the holder defining said rectangular and round holes being disposed substantially perpendicular to the axis of said actuating rod.

9. A cutting apparatus according to claim 7 wherein said rectangular hole comprises a slot having a width greater than the thickness of said thread-like body and less than the diamter of a projection, said round hole having a diameter greater than the diameter of a projection, the diameter of said round hole being insufficient for the passage of said threading member through said round hole.

10. A cutting apparatus according to claim 7 in which said actuating rod is slidably supported within a cylindrical holder.

11. A cutting apparatus according to claim 10, in which a spring is disposed between one end of said cylindrical holder and a contact member attached to one end of said actuating rod, and one end of said trigger contacts with said contact member.

12. A cutting apparatus according to claim 10 in which said cutting means is rotatably supported by a pin fixed on the inner wall of said cylindrical holder.

* * * * *